United States Patent [19]

Habib et al.

[11] Patent Number: 5,279,550
[45] Date of Patent: Jan. 18, 1994

[54] ORTHOPEDIC AUTOTRANSFUSION SYSTEM

[75] Inventors: Magdi F. Habib, Mission Viejo; George W. White, El Toro; Jack W. Brown, Santa Ana, all of Calif.

[73] Assignee: Gish Biomedical, Inc., Irvine, Calif.

[21] Appl. No.: 810,325

[22] Filed: Dec. 19, 1991

[51] Int. Cl.$^5$ .............................. A61M 5/00
[52] U.S. Cl. ................................ 604/38; 604/35; 604/4
[58] Field of Search ............... 604/4, 5, 6, 7, 35, 604/38, 45, 118, 121, 152, 154, 218, 37

[56] References Cited

U.S. PATENT DOCUMENTS

| | | | |
|---|---|---|---|
| 2,646,042 | 7/1953 | Hu | 604/38 |
| 3,515,127 | 6/1970 | Reymond | 604/152 X |
| 4,014,329 | 3/1977 | Welch et al. | 604/4 |
| 4,564,359 | 1/1986 | Rühland | 604/4 |
| 4,573,992 | 3/1986 | Marx | |
| 4,642,088 | 2/1987 | Günter | 604/4 |
| 4,642,093 | 2/1987 | Härle | 604/118 X |
| 4,671,786 | 6/1987 | Krug | 604/4 |
| 4,744,785 | 5/1988 | Rosenthal/Uhoch et al. | |
| 4,767,417 | 8/1988 | Boehringer et al. | |
| 4,994,022 | 2/1991 | Steffler et al. | 604/5 X |
| 5,133,703 | 7/1992 | Boehringer et al. | 604/4 X |

OTHER PUBLICATIONS

Solcotrans Plus Brochure.
The Solcotrans Orthopaedic Autotransfusion System Brochure.
Orthopaedic Autotransfusion System Orth-evac Brochure.
DePuy Closed Wound Drainage System Brochure.
Autovac 7900 Series by Boehringer Brochure.
Assessment of an Autotransfusion Device for Collection of Blood Researchers Ralph Bernstein and David Albert.
Stryker Surgical 215-28 ConstaVac Brochure.
Richards Solotrans Plus Drainage/Reinfusion System ST 6000 Series Brochure.

*Primary Examiner*—Robert A. Hafer
*Assistant Examiner*—Sam Rimell
*Attorney, Agent, or Firm*—George F. Bethel; Patience K. Bethel

[57] ABSTRACT

The following disclosure comprises a medical autotransfusion and blood drainage reservoir for withdrawing blood from the site of an operation under vacuum. A walled reservoir is connected to the operation site and a vacuum is drawn therein to draw fluids from the operation site. Vacuum is provided by a piston pump connected to check valves. The check valves allow for movement of the piston pump in one direction to discharge air therefrom, and in the other direction to withdraw air from the reservoir. Alternatively a spring driven bellows can be used to draw a vacuum with attendant check valves. The inlet of blood flow is through a filter. Blood is then capable of flowing outwardly to be reinfused by autotransfusion or reinfusion at a later time. Vacuum indication means and bleed off valves are included for maintenance of a proper vacuum.

15 Claims, 6 Drawing Sheets

ORTHOPEDIC AUTOTRANSFUSION SYSTEM

FIELD OF THE INVENTION

The field of this invention lies within the medical reinfusion and autotransfusion field. More specifically, it pertains to the utilization of a post operative drainage system which can be used for draining the area proximate an orthopedic procedure. The system for draining the area proximate the orthopedic procedure can be incorporated as an autotransfusion or reinfusion system for providing the patient with his or her own blood that has been drained from the operation area.

BACKGROUND OF THE INVENTION

Autotransfusion systems are now widely accepted. The reason why is that there is significant importance placed upon post operative blood collection and reinfusion. Consequently, various systems have been developed to incorporate the collection and reinfusion of blood into a patient's body.

Generally, the withdrawal of blood is under vacuum from an operation site. A preset suction is utilized to pull and drain blood from the operation site. In doing this, there is an effort to maintain red blood cells to protect them from potential hemolysis. Also, efforts are made to protect the tissue from being damaged at the operation site while at the same time insuring proper withdrawal of the blood from the site.

In order to effectuate this, various efforts have been attempted to withdraw the blood into a blood bag and then reinfuse it into a patient's body. The withdrawal is under vacuum which can be provided by a vacuum source such as the normal vacuum within a hospital environment. Such vacuum sources are usually provided through vacuum pumps connected to a series of pipes that can be accessed near a patient's bed or within an operating room procedural area. Also, it is known to drain wound or operation sites without the use of vacuum by merely allowing them to drain into a drainage tube on a gravity basis.

Most autotransfusion devices rely upon pulling blood from a wound or operation site that is suctioned directly into a holding area such as a blood bag or a reservoir. It is oftentimes filtered and mixed with an anti-coagulant and then reinfused directly from the same unit or from a blood bag.

The use of reinfused blood lowers the cost of transfusion from banked blood. This in turn lowers the expense to the patient. Additionally, problems such as typing, screening, risks such as AIDS or cross matching of banked blood is substantially eliminated if reinfused blood is transfused to the patient.

Such systems that are currently available are set forth in various patents. One of these patents is U.S. Pat. No. 4,573,992 entitled An Apparatus For Receiving and Reinfusing Blood by Guenter H. Marx assigned to Solco Basel AG. This particular device incorporates a concertina-like container which once filled is compressed to reinfuse the blood into a patient. In effect, it operates as an expansion chamber withdrawing the blood under vacuum, and then re-compressing the chamber for infusion. The device specifically lacks utility with respect to a constant vacuum source that can be used in adjacent relationship with it. It also lacks proper filters, and an overall configuration that can be adapted for use in an easy and facile manner during autotransfusion with respect to orthopedic operations.

A later development by the assignee of the foregoing patent incorporates an improved reservoir with an inherent vacuum source. However, it lacks a vacuum source and other features that make this invention functional and, capable of being implemented in a facile manner. For instance the vacuum source is a bulb, that when squeezed relies upon the resilience of the rubber in the bulb to expand and provide a vacuum. It furthermore does not provide a multiple displacement vacuum pump function as does this invention.

Another patent, namely U.S. Pat. No. 4,767,417 for a drainage device for collecting liquids from a body cavity assigned to Boehringer Laboratories incorporates a withdrawal system for withdrawing fluids from a wound or operation site. A particular vacuum maintenance regulation chamber is incorporated as well as a blood bag concept. However, in this particular case there is no integrated vacuum system as in the applicant's invention herein of the type necessary to perform an orthopedic autotransfusion function.

U.S. Pat. No. 4,744,785 entitled Autotransfusion System assigned to C. R. Bard sets forth a collection bottle that can be used for salvaging blood and reinfusing it. There is no inference as to an integrated vacuum system that can be utilized as that of the applicants herein.

From a reading of the literature and the general format of the prior art, it is believed that the applicants' invention sets forth an integrated vacuum system which is new and unobvious over the prior art.

The applicants' integrated vacuum system and reservoir as well as the entire autotransfusion system incorporates an integrated vacuum source in the form of a positive displacement manual piston pump. A wall vacuum access port is also provided as an alternative vacuum source. The integrated manual vacuum pump assures portability and a steady source of vacuum at the site through a displacement piston pump means which can be in the form of a syringe. The vacuum is regulated by a regulation system to be within the proper operational norms.

A bellows pump having a spring loaded interiorly expandable chamber with check valves can also serve as an alternative embodiment for this invention.

The invention further incorporates check valves in an arrangement for providing the vacuum and the exhaust by use of the integrated manual vacuum pump. The check valves are particularly adaptable and useful in their configuration and the circuit in which they have been placed.

Integrated filters in the reservoir are provided in order to filter the blood. The filter is emplaced with a pressed fitting and is entrapped on the top and bottom thereby, limiting the requirement for bonding.

A vacuum indicator is provided by this invention to visually indicate the amount of vacuum within the reservoir of the system. This is performed by a rubber bellows or other expandable device that moves an indicator with respect to a pre-established scale.

A filtered release valve and a vent is provided in order to establish a proper vacuum and relief when desired.

Further features include a quick disconnect means with a check valve as well as a blood bag attachment for using a blood bag in conjunction with the reservoir of the system. Also, injection and sampling ports are provided with the option of being able to inject or withdraw fluids such as anti-coagulants into the reservoir.

Based upon the foregoing advantages it is believed that this invention is a significant step over the prior art as to its form and functional features.

SUMMARY OF THE INVENTION

In summation, this invention incorporates an improved autotransfusion or reinfusion device for orthopedic and other medical operational uses incorporating an integrated manual piston vacuum pump.

More particularly, it incorporates an integrated manual vacuum pump in the form of a cylinder and piston. The vacuum pump is connected to a series of check valves arranged for both vacuum and exhaust by the pump. This allows for establishment of a vacuum on an integrated portable basis.

In the alternative a bellows pump can be utilized for the vacuum source. The bellows can be driven by an interior coil spring and provided with check valves for displacing interior air and drawing a vacuum.

An integrated filter assembly is provided in the reservoir and is pressed fit and inserted providing a seal without the need of bonding. The filter receives the blood and allows it to flow into the reservoir from which it can then flow outwardly for constant reinfusion or into a blood bag.

In order to establish a proper vacuum, a vacuum indicator is utilized in conjunction with a relief or bleed off valve. The vacuum indicator incorporates a rubber bellows or other expandable and contracting indicator in conjunction with a relief or bleed off valve. An indicator on the bellows is in adjacent relationship to a scale which shows the amount of vacuum within the reservoir.

To facilitate the operation, relief, valves, vents, quick disconnect and blood bag attachment connections are utilized. Also, injection and sampling ports provide the ability to place anticoagulants within the reservoir.

The entire system as set forth hereinafter is a significant step over the prior art in it's integrated and systematic function as shall be seen hereinafter.

DETAILED DESCRIPTION OF THE PREFERRED EMBODIMENTS

Figures 1, 4:
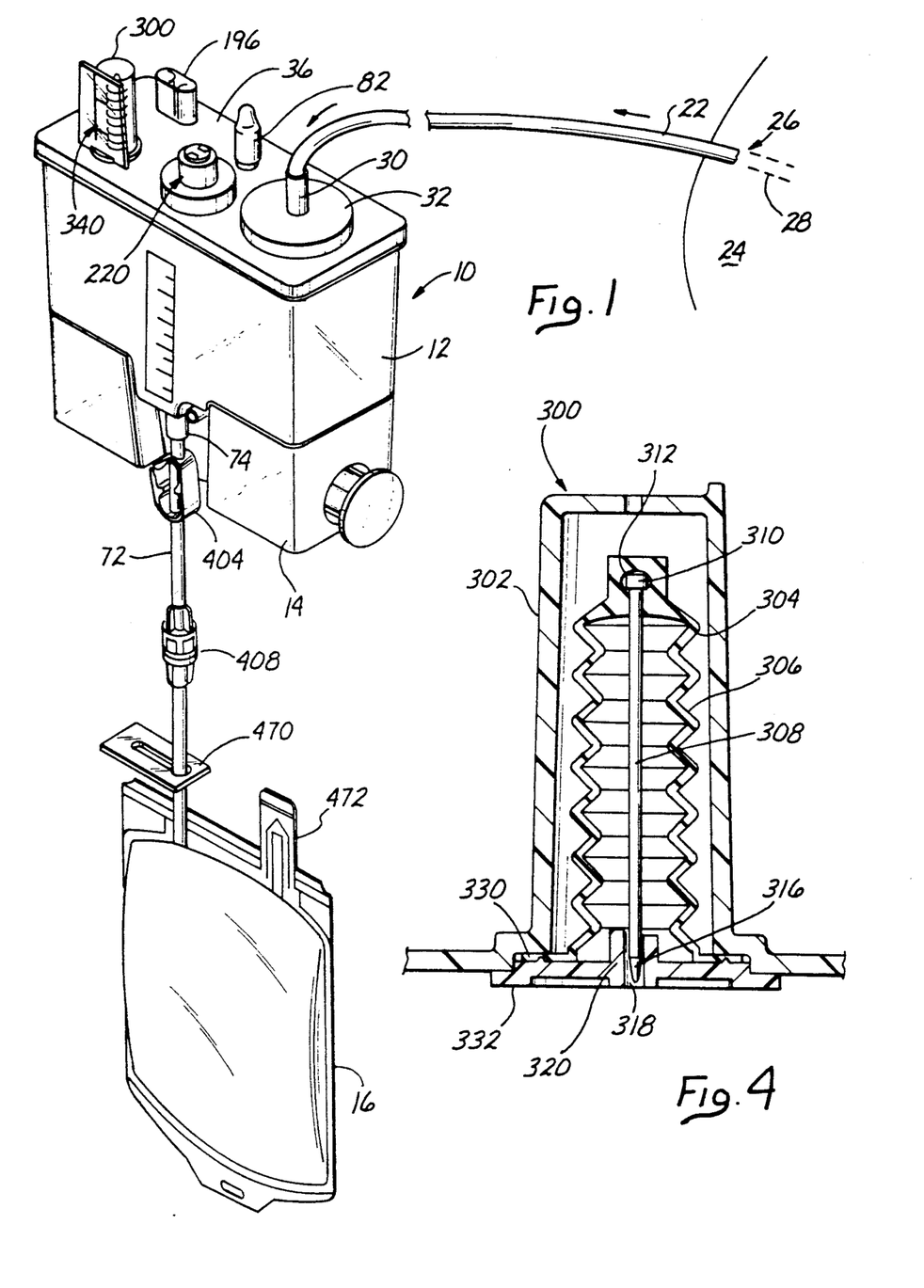
FIG. 1 shows a perspective view of the autotransfusion device of this invention with a blood bag connected thereto.
FIG. 4 shows a midline cross-sectional view of the vacuum indicator.

FIG. 1 shows the autotransfusion device labeled 10 with a body having an interior cavity forming a reservoir 12. The body forming the reservoir 12 is made of a fixed non-collapsible material such as a polycarbonate or other material that is not prone to collapsing. This is because it must be capable or sustaining a vacuum interiorly thereof. Other considerations can be formulated to provide variously shaped vacuum chambers to perform the function of the reservoir 12. In most cases it is preferred that a non-collapsible material be utilized for the reservoir to prevent the collapse of the walls.

The reservoir 12 is provided with an underlying cover shroud or body 14. The underlying cover or shroud 14 covers many of the operative elements of the invention which shall be expanded upon. Inasmuch as it is not subject to the requirement for the maintenance of a vacuum, it can be made from a lighter plastic such as an abs plastic.

Figure 2:
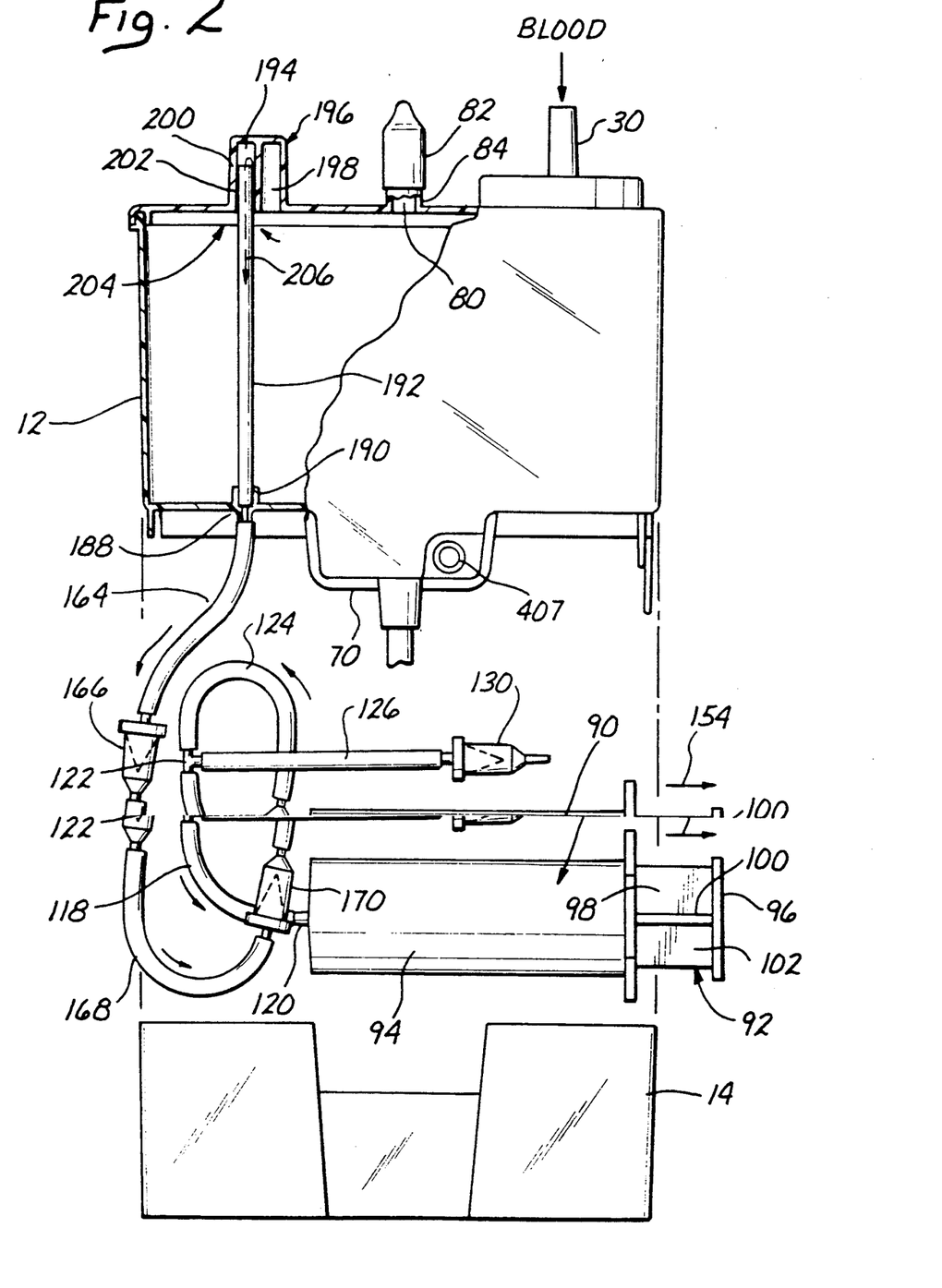
FIG. 2 shows a partially sectioned and exploded view of the autotransfusion unit of this invention with the direction of vacuum flow being established through movement of the piston of the vacuum pump.

The lower housing or cover 14 is generally bonded to the reservoir 12 as can be seen more particularly in FIG. 2 in the exploded view.

FIG. 1 also illustrates the utilization of a blood bag 16 which can form a receptacle for the receipt of blood from the reservoir or body 12 in which it is collected. This blood bag 16 can also be substituted by way of a direct infusion tube 18 shown in FIG. 1B. This connecting infusion tube 18 takes the place of the blood bag so that infusion can take place from reservoir 12 directly to the patient.

Looking again more particularly at FIG. 1, it can be seen that a drainage line 22 is shown. The drainage line is connected to a trocar and inserted into a patients body generally shown as 24. The insertion is near the operation site or in the general vicinity of where an orthopedic operation has taken place. The drainage line 22 connected to the operation site is such wherein it has been inserted into the body. It includes a tube 26 having openings 28 therein for the receipt of drainage from the site of the orthopedic operation or procedure.

The drainage line 22 is shown extending to an inlet port 30. The inlet port 30 is connected to a flange or recess 32 that can be formed as a boss on the top or lid of the unit 10. The flange or recess 32 can be seen more clearly in the cross-sectional view of FIG. 7.

Figure 7:
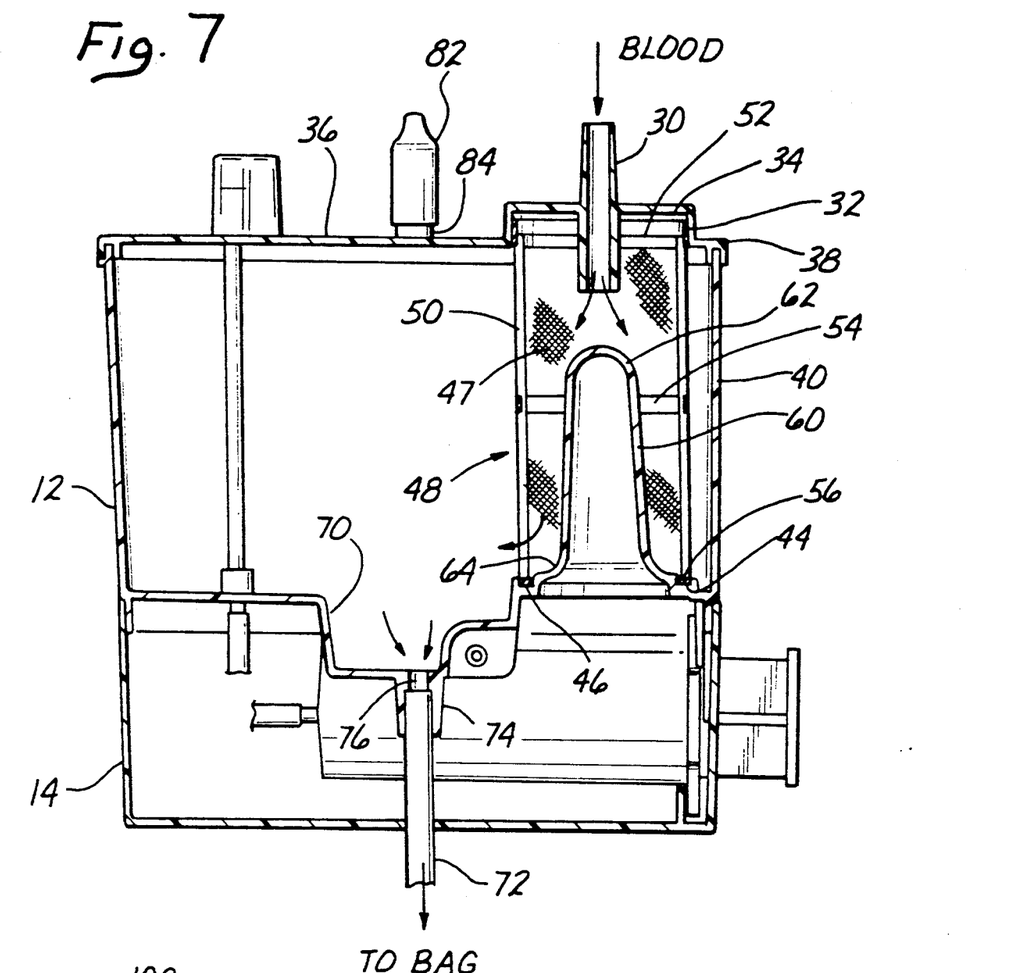
FIG. 7 shows a sectional view of the autotransfusion reservoir of this invention detailing the showing of the filter and the flow of blood.

The flange 32 or recess is formed with it's interior boss 34 within the top portion or lid 36 of the body 12. The top portion or lid 36 has been formed and molded in such a manner as to provide for a groove or channel 38 around the exterior portion. The groove or channel 38 is seated over sidewalls 40 of the body 12 forming the reservoir.

The inlet 30 extends interiorly of the cover 36 and downwardly beyond the flange or interior boss 34 to provide for the flow of blood into a cylindrical filter 48. The cylindrical filter comprises a filter which has been pressed fit at it's upper portion into the rounded boss or recess 34 to provide a seal.

At the lower portion of the body with the reservoir 12 is formed an interior step with a groove 44 at the base thereof forming a circular channel 46. The groove 44 forming the circular channel 46 receives the other end of the filter 48.

In order to form the walls of the cylindrical filter 48, a filter material 47 in the way of a nylon mesh approximately 95 microns in porosity is utilized or other suitable filter material. The nylon filter can be anywhere from 20 to 250 microns in porosity as to the openings thereof.

In order to rigidify the cylindrical nylon mesh 47, a ribbed basket is utilized having uprights or stays 50 and hoop like portions 52, 54 and 56 which circumscribe the filter and are supported by four uprights or stays 50. With this reinforcement the filter material 47 is not prone to collapse and can sustain itself under normal operational conditions.

As previously stated, the filter 48 is pressed fit into the upper flange or boss 32 and the circular channel 44 without the necessity of an adhesive. Without the use of adhesive the avoidance of disparate and foreign material is maintained. This prevents the chance of adhesive sluffing off or contaminating any portion of the interior blood filter area. However, in certain instances an adhesive can be used without any deleterious effects.

A volume displacer forming a blood flow spreader 60 is formed of a rounded plastic conical form. It has a rounded top 62 flaring downwardly into a bell shaped bottom portion 64 which is formed with a step and grove 44 therein to provide the channel 46.

When blood is flowing, it flows from the inlet tube 22 to the inlet port 30 that extends interiorly of the reservoir 12. It is then spread over the volume displacer's smooth rounded top 62 whence it then flows through the filter sidewalls or material 47, and downwardly into the bottom of the reservoir 12. This general flow pattern can be seen in the flow direction indicated by the arrows in FIGS. 1, 1B, and FIG. 7.

Again looking more particularly at FIG. 7 and the other figures pertaining thereto, it can be seen that the reservoir 12 has a sump 70. The sump 70 is a low point within the reservoir 12 in order to receive the blood that flows through the filter 48. This 70 sump is in turn connected to a tubular conduit 72. The tubular conduit 72 can be formed as a conduit shown in FIG. 7 pressed fit or adhered into a flange or extension 74 having an internal opening 76 which flows into the tubular conduit 72.

In the alternative, the conduit 72 can be adhered by way of an adhesive, solvent, or bonded by way of RF welding or provided in any other manner in order to secure itself to the sump 70. The conduit 72 can also be a slip fit elastomeric type of tubular member slipping onto a male connector conduit in the alternative to the flange 74 or extension 74.

The autotransfusion unit 10 relies generally upon a vacuum in order to provide the autotransfusion function and withdrawal of blood from the operation site 24 through the tube 22. In order to provide vacuum, many prior art devices that performed similar functions relied upon a wall vacuum port. The wall vacuum port is also provided by this invention seen as port 80. Port 80 has an opening which is covered by a non vented nozzle cover 82, the port 80 is formed from an upstanding tubular portion 84. The nozzle cover 82 is in the form of a plastic, elastomeric, or other material that has been formed to fit over the port 80 in a tightly sealed manner.

A vast improvement of this invention is the feature of its integrated vacuum system. The integrated vacuum system does not rely upon the hospital wall vacuum that is normally available in a hospital environment from a vacuum source such as a vacuum pump connected to each respective room by a series of interior building pipes. Normally, as previously stated, the prior art devices relied upon the utilization of such a wall vacuum or adjacent motorized vacuum to draw vacuum through the opening 80 which is covered by the cap 82 of this invention. The nozzle cover or cap 82 is such where it is retained in place during normal operation of the integrated vacuum system of this invention.

Figure 3:
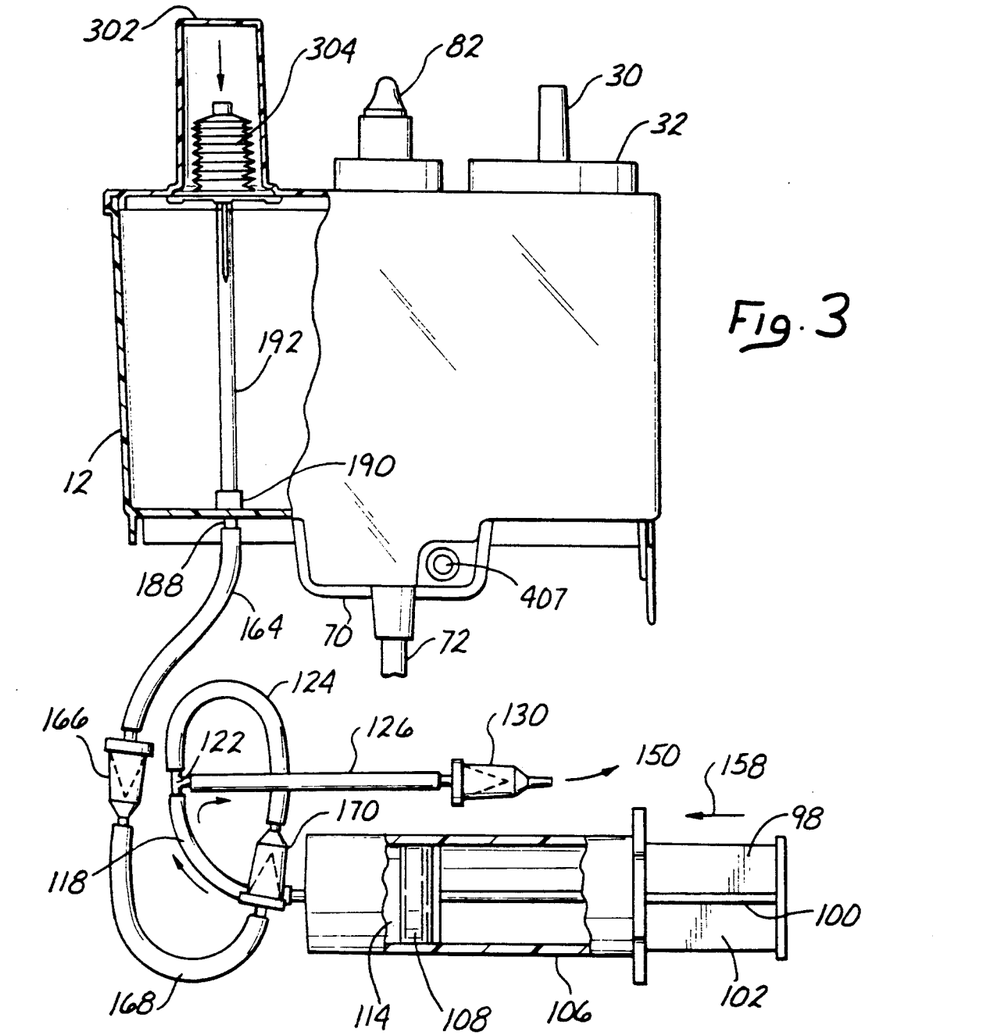
FIG. 3 shows a fragmented sectional view of the autotransfusion unit of this invention with the piston moving to discharge air from the interior of it's surrounding cylinder prior to pulling backwardly into a vacuum mode.

Looking more specifically at FIGS. 2 and 3 it can be seen as to how the vacuum is implemented. FIGS. 2 and 3 show a positive displacement hand operated piston pump 90. The positive displacement pump 90 incorporates a plunger or piston drive 92. The respective pump 90 with its plunger 92 or piston drive is formed with a cylindrical walled portion 94 in which the plunger 92 is seated.

The plunger 92 has an enlarged portion or disk 96 forming a hand grip. The disk 96 is formed on a cruciform ribbed member comprising cruciform ribs 98, 100, and 102. The fourth cruciform rib is hidden from view but is diametrically opposite from the rib 100.

The plunger 92 can be of any particular form so long as it provides positive displacement of the air within the system as will be detailed hereinafter. The positive displacement of the air can be performed by a plunger that is lever operated. For instance it can be on a pin to allow a lever handle to push a piston or plunger inwardly and outwardly. It can be formed with a pivotal hand pump, an over center toggle action or any other suitable positive displacement drive means to displace air from an enclosure such as the cylinder 94.

The cylinder 94 has cylinder walls 106. The cylinder walls 106 receive a piston element 108 connected to the plunger or piston drive 92. The piston element can be in the form of a piston, stopper or plug like element which substantially seals against the walls 106 of the cylinder 94.

Figure 8:
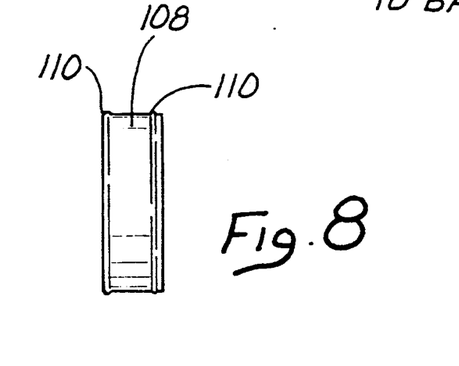
FIG. 8 shows a view of the piston seal and ring of the piston for sealing purposes.

The stopper or piston 108 incorporates sealing or piston rings 110. These can be seen more clearly in FIG. 8 wherein the piston 108 is seen with the rings 110 thereof surrounding the piston or stopper 108. Any other suitable sealing means can be utilized so long as a vacuum type seal is incorporated so as to allow withdrawal of air or other fluid or gaseous media from the reservoir 12.

A space 114 is shown ahead of the piston 108. This space 114 is within the cylinder walls 106 and is in turn connected to a tubular circuit comprising a first tube 118 connected thereto by means of a friction fit over an outlet 120 of the cylinder 94. This is in turn directly connected to the area 114 in front of the piston 108.

The tube 118 is in turn connected to a T or Y 122. The T or Y 122 branches into a first tube 124 connected thereto and a second tube 126. The two respective tubes 124 and 126 are frictionally fit on the T 122. They can be connected in any other suitable manner such as by means of adhesive, insert molded, RF welded or a completely injection molded device incorporating the T 122, tubes 118, 124 and 126. The T 122 can also be a Y connection or any other branch configuration allowing the flow through two branches as shown, namely tubes 124 and 126 which may be formed as branches or conduits of any suitable configuration having the valving functions detailed hereinafter.

Figure 6:
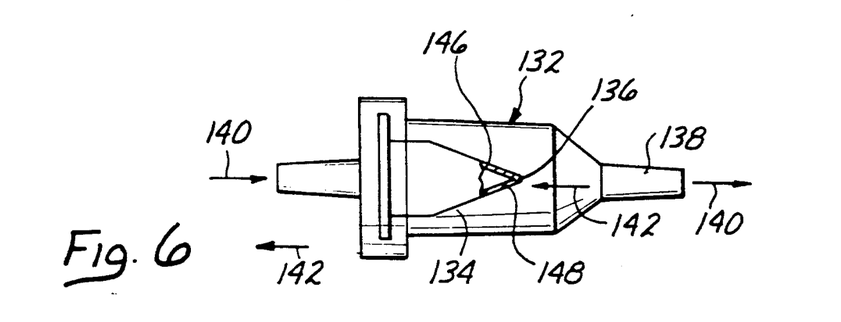
FIG. 6 shows a detailed sectional view of one of the series of duck bill valves that provide the discharge of air and vacuum through the vacuum pump.

The tube 126 is connected to a duck bill valve 130 The duck bill valve 130 and the other duck bill valves that will be described hereinafter are exemplified by FIG. 6. Duck bill valve 132 has an elastomeric duck billed member 134 formed with an opening or slit 136 that can flap open and close when positive pressure or negative pressure is respectively seen at the slit. The duck bill valve 132 has a connection 138 for flow in the direction of arrow 140 through the duck bill valve. Flow in the opposite direction namely in the direction of arrow 142 is checked by virtue of the elastomeric walls 146 and 148 closing on themselves to prevent flow in the direction of arrow 142 through the opening or slit 136. Consequently, the duck bill valve serves as a check when pressure or flow is seen in the direction of arrow 142 and as an opened passage when seen in the direction of arrow 140.

The duck bill valve 132 forming the valve 130 allows for flow as seen in FIG. 3 in the direction of arrow 150. The reason for this is that displacement from the space 114 of the cylinder 94 must take place before vacuum can be provided to the reservoir 12. This is true unless the piston and plunger 92 are in a position such as in FIG. 2 to be moved in the direction of arrow 154.

In order to displace the air from the cylinder 94 the piston is moved in the direction of arrow 158. As it is moved in the direction of arrow 158 it displaces the air in the direction of arrow 150. This can be seen by the arrows flowing from the cylinder 94 and through the duck bill valve 130 which serves as a check valve in the opposite direction when a vacuum is drawn.

Looking more particularly at FIG. 2, it can be seen wherein the plunger or piston drive 92 is functioning in the vacuum mode. In this manner, it is moving so as to draw vacuum from the reservoir 12. This is done through a tubular connection provided by tube 164 connected to a first duck bill valve 166 and a tube 168 connected to a second duck bill valve 170. The second valve is for a backup safety function. The second duck bill valve 170 is connected to the tube 124 through the Y 122 to the tube 118 and then to the cylinder 94. Thus as the piston 108 connected to the drive 92 is drawn in the direction of arrow 154 it provides a vacuum through the duck bill valves 166 and 170 opening in the flow direction as seen in the direction of the arrows shown in FIG. 2. The movement of the piston 108 of the plunger or drive 92 is in the direction of arrow 154.

In this vacuum drawing capacity, the duck bill valve 130 is in the direction whereby the vacuum flow through tubes 124 and 118 as seen at T 122 is such to draw down the elastomeric portions 146 and 148 and close the slit 136 of the duck bill valve to prevent flow into the system.

Instead of duck bill valves in whole or in part, disc valves or flapper valves can be substituted therefor. This pertains to all the embodiments herein with both the piston pump and the alternative bellows system described in FIGS. 9 through 12.

Instead of the duck bill valves 130 and vacuum circuit for pumping down reservoir 12, a piston having check valves on its faces can be used. Also other means to check flow on either side of the piston can be used.

For instance piston 108 can incorporate a one way check valve for one way flow in either direction of movement. In this manner, tube 164 would be connected directly to connection 120 to allow reciprocating action of piston 108 to provide the vacuum.

Tube 164 is connected to an inlet 188. The inlet 188 is a downward stub having an opening as can be seen in FIG. 2 connected to a round recess. The recess is formed from a circular cylindrical base walled portion 190 formed within the wall of the reservoir 12. The circular base member 190 receives a tube or straw 192 extending upwardly therefrom as seen in FIG. 2.

The tube or straw 192 is received within an upper opening 194. The opening 194 is formed in an upstanding boss portion 196 having a second opening 198 connected to the interior of the reservoir 12.

The tube 192 allows vacuum to be provided in the direction of the arrows of FIG. 2. The vacuum flows between the walls of the opening 194 namely walls 200 and an interfacial space 202 through which vacuum in the direction of arrows 204 can be provided to draw vacuum downwardly in the direction of arrow 206. This downwardly directed vacuum in the direction of arrow 206 is accomplished when the piston 108 is drawn in the direction of arrow 154.

The reason for the straw or the tube 192 is to accommodate the vacuum being drawn in the direction of arrow 206 without the effect of blood flowing into the tube 192 and blocking it. By placing the conduit 192 upwardly into the opening 194, the blood in the reservoir 12 will generally not block the vacuum provided through the tube 192. The tube 192 will instead remain with an open port in the space 194 so that a vacuum can be drawn through the interface 202.

FIGS. 9 through 12 show an alternative pump embodiment for substituting the piston displacement pump 90 of this invention. In particular, the top 36 is extended with an overlying portion or ledge 600. The ledge 600 incorporates a support for the bellows of this invention which serves to provide the vacuum.

Figures 9, 10, 11, 12:
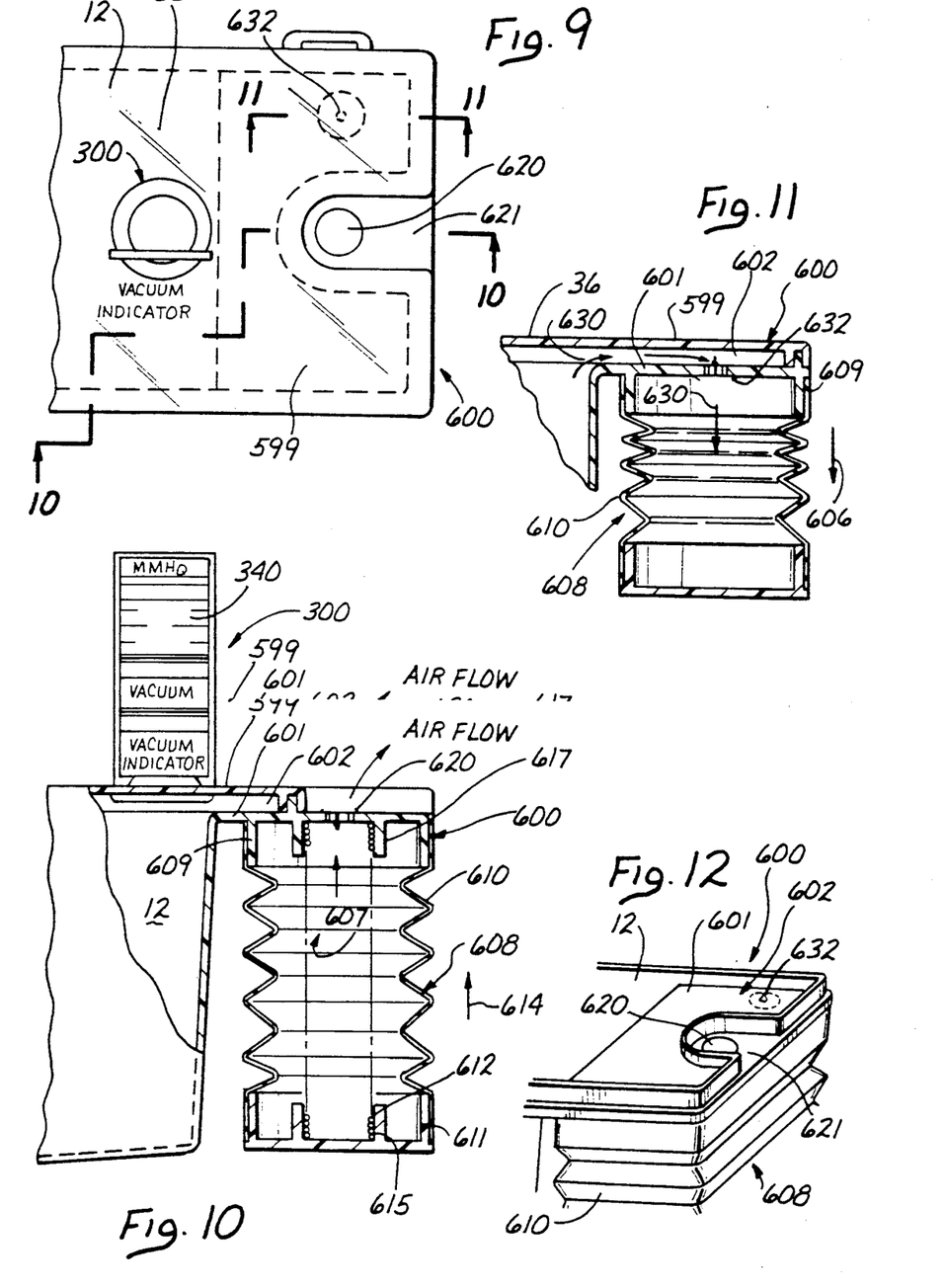
FIG. 9 shows a top plan view of an alternative embodiment of this invention incorporating a bellows pump.
FIG. 10 shows a sectional view of the bellows pump along lines 10—10 of FIG. 9.
FIG. 11 shows a sectional view of the bellows pump along lines 11—11 of FIG. 9.
FIG. 12 shows a perspective view of the bellows of the alternative embodiment with the top cover removed.

The vacuum indicator is shown analogous to vacuum indicator 300, to serve the function of indicating on the scale 340 how much vacuum is being drawn.

Looking more particularly at the ledge 600 it can be seen that it is formed in conjunction with an extension of the reservoir 12 walls in the form of a lower wall 601 The reservoir walls extend outwardly as a pair of walls 599 and 601 to form a sealed small space 602 in conjunction with the reservoir 12.

This small space 602 allows the interior of a rectangular bellows 608 to draw a vacuum in the direction of arrow 630 downwardly into the bellows when it expands. When the bellows 608 is in its expansion mode it draws air to form a vacuum through space 602 into the bellows and holds the air until discharged through a check valve or flapper valve 620 in the direction of arrow 607. This is due to the expansion of the bellows in the direction of arrow 606 which constitutes downward directional movement.

The bellows 608 can be seen formed of an elastomeric sidewall 610 having ribs and valleys thereof to provide for expansion and contraction. Interiorly of the bellows 608 is a coil spring 612 which provides the force for expanding the bellows 608. The coil spring is shown expanded in FIG. 10 and contracted in FIG. 11.

The contraction in FIG. 11 is such wherein the spring 612 can drive the bellows 608 downwardly in the direction of arrow 606 as shown in FIG. 11. When the bellows 608 is driven upwardly as in FIG. 10 in the direction of arrow 614, air is expelled through a one way check valve 620, which is a disc or flapper valve in the flow direction of arrow 607. The valve 620 is shown exposed to atmosphere within an indentation or space 621 that can have a cover overlying it, yet maintaining a space for bleeding air through valve 620 to the atmosphere.

The bellows 608 is seated around a circular flange 609, and upright cup shaped flange 611 at its base. The spring 612 is seated in a smaller circular flange 615 in the base and an upper circular flange 617.

As previously stated the bellows 608 is connected to the air flow passage 602 by means of a flapper or disc valve 620. The flapper or disc valve 620 allows air flow outwardly in the direction of arrow 607. Fundamentally it serves as a one way valve so that flow can only be in the direction of arrow 607.

After contraction and air has been discharged through valve 620 as seen in FIG. 11, the bellows 608 can expand in the direction of arrow 606 as driven by the spring 612. In this mode, it draws air from the reservoir 12 in the direction of arrow 630. This is caused by an opening of a disc or flapper valve 632 that opens to allow the drawing of air in the reservoir 12 into the bellows 608. This air in the bellows 608 can then be expelled upon pushing and contraction in the direction of arrow 614.

As a consequence, this invention allows for a spring loaded bellows pumping of the reservoir 12 so that flow can take place in the direction of arrow 607 outwardly from the bellows 608 through the one way valve 620. Thereafter, air from the reservoir 12 connected through passage 602 can be drawn inwardly in the direction of arrow 630 through the valve 632 as the bellows 608 expands by the spring pressure of spring 612.

Figures 1B, 5:
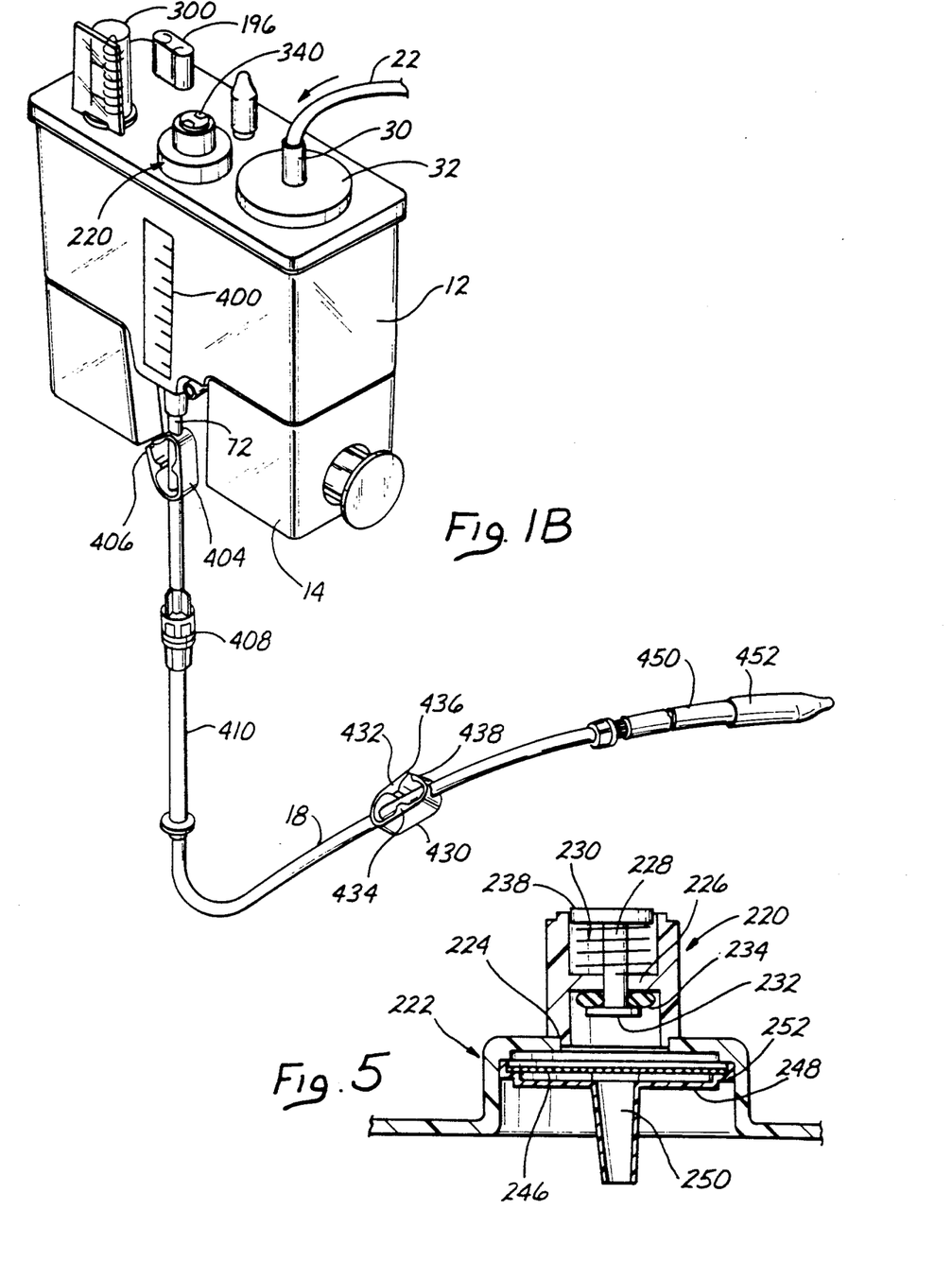
FIG. 1B shows an analogous view to FIG. 1 in the way of a perspective view wherein a reinfusion connection tube has been connected to the autotransfusion unit.
FIG. 5 shows a sectional view of the relief valve and vent connected to the reservoir of this invention.

The vacuum applied in the reservoir 12 is regulated by means of a relief and venting valve detailed in FIG. 5. The relief and venting valve is shown as a relief valve 220. The relief valve 220 can be seen formed and mounted in a boss 222 formed in the upper portion of the cover 36 of the reservoir. The upper portion or reservoir lid 36 incorporating the boss 222 has the valve 220 formed in an opening 224 by virtue of a stepped seating and adhesion thereof by an appropriate adhesive or other bonding technique.

The walls of the relief valve 220 have a web 226 across the midsection thereof with a stem 228 and a spring 230 holding the stem 228 upwardly. The stem 228 has a lower disk 232 connected thereto which sustains and retains an 0 ring 234. The O ring 234 is used to seal the relief valve and vent.

When relief or venting is required, the face of the relief valve in the form of a split disk 238 having a passage therethrough is pressed downwardly to allow the flow of air into the vacuum regulated reservoir 12. When the button or relief valve 238 which is opened to atmosphere is pressed downwardly it allows a relief of the seal 234. This provides for admission of atmospheric pressure into the chamber of the reservoir 12.

In order to aid in the sealing of the reservoir 12 from atmospheric contaminants, a filter 246 is provided. The filter 246 is in the form of a filter disk spanning a cylindrically lipped disk 248 having a downwardly directed port 250. The port 250 extends therefrom to allow the flow of air through the filter while at the same time preventing contaminants from being introduced into the blood supply within the reservoir 12. The disk 248 is stepped with a minor step 252 or circular ledge having a lip to support the filter disk 246. The disk 248 can be sealed into the boss 222 against a ledge interiorly thereof.

In order to monitor the amount of vacuum in the interior of the reservoir 12, a vacuum indicator 300 is provided. The vacuum indicator 300 incorporates a rubberized bellows within an upstanding chamber. More particularly, an upstanding chamber 302 is formed within the top lid 36 of the reservoir cover. This upstanding chamber 302 has a bellows 304 therein. The cylindrical bellows 304 is formed of an elastomer such as a rubber material with undulations 306 formed from cylindrical lands and grooves therein. The rubber can be a kraton or santoprene type of synthetic rubber to allow for the expansion and contraction of the bellows 304.

In order to support the bellows, a central pin 308 is provided with a head 310 fitted within an opening 312 of the bellows 304. The head of the pin 310 within the opening 312 allows for the pin 308 to reside therein while at the same time supporting the bellows in it's elastomeric flexible nature while maintaining its upright configuration. Without the pin 308, the bellows might contract in a non-uniform non-axial manner and not be driven uniformly upwardly and downwardly to indicate the extent of the vacuum.

The pin 308 has a reduced end 316 passing through a passage 318 provided by a cylindrical sidewall 320. The bellows 304 terminates in a wide flared base 330 which is seated against a disk 332. This holds the cylindrical base 330 of the bellows in tight juxtaposition and creates a seal to the upstanding walled chamber 302.

When a vacuum is sensed through the opening 318 in communication with the reservoir 12, the bellows 304 moves downwardly by contraction. The top of the bellows 304 can be read against a gauge reading having gauge markings such as those seen on gauge scale 340. The gauge scale 340 allows for the top of the bellows 304 to indicate how much vacuum is being maintained in the reservoir 12. The showing of FIG. 3 illustrates the bellows 304 when it contracts upon itself, to indicate the degree of vacuum in the reservoir 12.

In order to prevent hemolysis, the vacuum should be regulated as to not exceed approximately 100 mmHg. If approximately 100 mmHg of vacuum is exceeded in the reservoir 12, the relief valve shown generally as relief valve 220 is drawn inwardly by virtue of the spring compression pressure of spring 230 being overcome. This is due to the spring compression resilience of spring 230 being set to be overcome to allow the flow of atmospheric pressure around the O ring 234. This thereby relieves the interior of the reservoir 12 to be within a pre-established vacuum range.

From the foregoing, it can be seen that the vacuum can be created on a controlled basis within the reservoir 12. This is done by drawing the piston 92 in the direction of arrow 154 in order to positively draw a vacuum and pull down a vacuum in the reservoir 12. When the piston 92 is pushed in the other direction of arrow 158 it drives the air that is pulled from the reservoir 12 outwardly in the direction of arrow 150 through the duck bill valve 130. This allows for a vacuum pumping down so to speak by the positive displacement pump drawing the interior of the reservoir 12 into a vacuum state.

The net result is when a reciprocating movement of the plunger 92 and stopper or piston 108 takes place backwardly and forwardly, a vacuum can be achieved. The vacuum can be increased to a certain level until an appropriate vacuum is achieved as can be seen in FIG. 3 under the vacuum state as indicated by the contracted bellows 304.

In FIG. 3 it can be seen that the bellows 304 are drawn downwardly in the direction of the arrow with the stem 308 extending to within the interior of the reservoir chamber 12. This interior vacuum is sustained until either the relief valve 220 allows atmospheric pressure to enter the relief valve top 238, or is displaced downwardly by manual articulation. As can be seen from the drawings of FIGS. 1 and 1B the top of the relief valve 220 has openings to allow for the passage of air through the relief valve disk 238.

Upon a filling of the reservoir 12, the blood within the reservoir as gauged by a blood volume indicator 400 can be passed through the tube 72 downwardly so long as clamp 404 is relieved. Clamp 404 is a Halkey or compression type of clamp that is fundamentally a pressure clamp formed by a spring lock 406 which is well known in the art.

While the blood is in the reservoir 12, an infusion port 407 can be utilized to infuse anticoagulant in the blood. Also sampling can be undertaken of the blood in the reservoir 12. The port is covered by a membrane or septum of natural rubber through which a needle can pass and leave a sealed septum after withdrawal.

A threaded connector 408 is shown by which the tube 72 can be connected to a larger or smaller tube 410 so that a separately sized tube can be utilized.

When a larger tube 410 is being utilized, it can be connected to the reinfusion tube 18. Tube 18 is also controlled to stop or start reinfusion through a Halkey clamp 430 having a spring bias which serves to clamp by two ridges 432 and 434. These ridges clamp the diameter of tube 18 when the tip 436 is secured under a locking ledge 438. This is the same manner in which the Halkey clamp 404 functions.

The reinfusion can take place through an intravenous tube provided through a reinfusion coupling 450. The coupling 450 is covered by a nozzle cover 452 until it is placed in use.

When looking more particularly at FIG. 1, it can be seen that the coupling 408 connects a blood bag 16 that can be provided with a clamp to close the blood bag after filling namely by clamp 470. The blood bag can then be utilized with its reinfusion port 472. The port 472 is opened and allowed to reinfuse the patients blood intravenously that has been drawn from the operation site 24.

Continuous autotransfusion can be undertaken by disconnecting the blood bag 16 and attaching a continuous autotransfusion device as that shown in FIG. 1B.

Regardless of how the autotransfusion or reinfusion takes place, it should be understood that the invention hereof is a significant step over the art in providing a users blood for reinfusion and autotransfusion purposes. Thus, the claims should be broadly read as seen hereinafter with respect to their scope and spirit.

We claim:

1. A medical device for withdrawing blood from the site of an operation by a tube which has been connected for drainage therefrom comprising:
   a reservoir with walls of sufficient strength to resist collapse under a given vacuum;
   an inlet port of said reservoir for connection of the tube connected to the operation site;
   an outlet means from said reservoir;
   a hand operated piston type displacement pump in connected relationship to said reservoir for withdrawing air from said reservoir and creating an attendant vacuum,
   means for reciprocating said piston type displacement pump; and,
   means for checking the introduction of air into the reservoir after a displacement thereof has taken place.

2. The device as claimed in claim 1 further comprising:
   means connected to said displacement pump to allow the driving of air from said pump in the form of a check valve allowing flow therefrom without flow into said reservoir; and,
   check valve means to allow for said pump to draw air from said reservoir while checking air from the atmosphere.

3. The device as claimed in claim 2 wherein:
   said check valves are formed as duck bill valves.

4. The device as claimed in claim 1 further comprising:
   means to relieve vacuum within said reservoir.

5. The device as claimed in claim 1 further comprising:
   a filter surrounding the inlet in said reservoir for filtering blood flowing thereinto.

6. The device as claimed in claim 5 further comprising:
   a volume displacement flow spreader proximate to said inlet for allowing blood to flow thereover before it passes through said filter.

7. The device as claimed in claim 1 further comprising:
   a vacuum indicator in the form of an expandable and contractable member having an interior opening connected to said reservoir so that as said member expands or contracts its position can be compared to a scale indicating relative vacuum within said reservoir.

8. The device as claimed in claim 1 wherein:
   said displacement pump is connected to a conduit extending above a pre-established level of reservoir blood volume to aid in the prevention of clogging the vacuum connection to said displacement pump.

9. A device for providing autotransfusion and/or withdrawal of fluids from the site of an operation wherein an inlet tube has been connected to the site of the operation comprising:
   a walled reservoir having a bottom, and a top thereto;
   means for connecting the inlet tube from an operation site to said reservoir;
   means for filtering the flow of blood from the inlet tube into the reservoir;
   a piston pump connected to said reservoir having respective check valves to provide a discharge from said pump of air therein to atmosphere and withdrawal of air from said reservoir to provide a vacuum therein; and, means for reciprocating said piston pump to provide the respective discharge and withdrawal functions.

10. The device as claimed in claim 9 further comprising:
a disc valve oriented for discharge of air by said piston pump when the piston moves; and
at least one second disc valve for preventing the flow of air into the reservoir and wherein said disc valves are connected in a branched configuration to allow checking by one valve while the other valve allows flow.

11. The device as claimed in claim 9 further comprising:
means for indicating the vacuum within said reservoir in fluidly connected relationship thereto.

12. The device as claimed in claim 11 further comprising:
an elastomeric expandable and contractable member forming said means for indicating vacuum within said reservoir which expands and contracts for the indication of relative vacuum within said reservoir.

13. The device as claimed in claim 9 further comprising:
a relief valve connected to said reservoir comprising a spring loaded valve to permit the introduction of atmospheric air into said reservoir at a given vacuum; and,
filtration means for preventing the introduction of contaminants through said relief valve into said reservoir.

14. The device as claimed in claim 11 wherein said vacuum indicating means comprises:
a bellows having the interior thereof connected in sealed relationship to the interior of said reservoir; and,
means for stabilizing the movement of said bellows for movement along its longitudinal length.

15. The method of withdrawing blood from the site of an operation by a tube which is connected in proximate relationship to said site comprising:
providing a reservoir with walls of sufficient strength to resist collapse under a given vacuum;
connecting said reservoir to said operation site by means of a tube;
providing a hand operated displacement piston pump connected to said reservoir;
moving said hand operated pump for purposes of creating a vacuum;
checking flow from said hand operated pump into said reservoir when said pump is moving to discharge air from said pump for discharge to atmosphere; and,
checking atmospheric flow into said pump when said pump is drawing vacuum from said reservoir.

* * * * *